US012782341B2

(12) United States Patent
Chen et al.

(10) Patent No.: US 12,782,341 B2
(45) Date of Patent: Nov. 3, 2026

(54) METHOD FOR EXTRACTING AND IDENTIFYING POLYSACCHARIDE FROM COMPLEX SAMPLE

(71) Applicant: ZHEJIANG UNIVERSITY, Hangzhou City (CN)

(72) Inventors: Shiguo Chen, Hangzhou City (CN); Jinghua Wu, Hangzhou City (CN); Kai Zhu, Hangzhou City (CN); Xingqian Ye, Hangzhou City (CN)

(73) Assignee: ZHEJIANG UNIVERSITY, Hangzhou City (CN)

( * ) Notice: Subject to any disclaimer, the term of this patent is extended or adjusted under 35 U.S.C. 154(b) by 504 days.

(21) Appl. No.: 18/521,208

(22) Filed: Nov. 28, 2023

(65) Prior Publication Data

US 2025/0172545 A1 May 29, 2025

(51) Int. Cl.

| | |
|---|---|
| ***G01N 33/53*** | (2006.01) |
| ***C08B 37/08*** | (2006.01) |
| ***G01N 1/34*** | (2006.01) |
| ***G01N 30/00*** | (2006.01) |
| ***G01N 33/00*** | (2006.01) |

(52) U.S. Cl.

CPC ....... *G01N 33/5308* (2013.01); *C08B 37/003* (2013.01); *G01N 1/34* (2013.01); *G01N 33/0098* (2013.01); *G01N 2030/009* (2013.01); *G01N 2333/926* (2013.01); *G01N 2400/10* (2013.01)

(58) Field of Classification Search

None

See application file for complete search history.

(56) References Cited

PUBLICATIONS

Wang et al., "Simultaneous determination of fructose, glucose, and sucrose by solid phase extraction-liquid chromatographs-tandem mass spectrometry and its application to source and adulteration analysis of sucrose in tea" J. Food Comp . Anal. v. 96 No. 103730, pp. 1-9, DOI:10.1016/j.jfca.2020.103730 (Year: 2021).*

Yilamz et al., "Optimization of Hydrophilic-Lipophilic Balance Solid-Phase Extraction of Phthalates in Pharmaceutical Preparations" Journal of the Turkish Chemical Society vol. 6(3) pp. 271-280, DOI:10.18596/jotcsa.526124 (Year: 2019).*

Hitchcock et al., "Optimized extraction of glycosaminoglycans from normal and osteoarthritic cartilage for glycomics profiling" Glycobiology vol. 17 No. 1 pp. 25-35, doi:10.1093/glycob/cwl046 (Year: 2006).*

Vieira et al., "Glycomic Analysis of Tear and Saliva in Ocular Rosacea Patients: The Search for a Biomarker" The Ocular Surface vol. 10 No. 3 pp. 184-192 (Year: 2012).*

* cited by examiner

*Primary Examiner* — Andrea Olson

(74) *Attorney, Agent, or Firm* — BROOKS KUSHMAN P.C.

(57) ABSTRACT

A method for extracting and identifying a polysaccharide from a complex sample. The method includes: subjecting a complex sample to be treated to sterilization and enzyme deactivation to obtain a system, and subjecting the system to solid-liquid separation to obtain a sterilization and enzyme deactivation-treated solution; deproteinizing the sterilization and enzyme deactivation-treated solution to obtain a deproteinized solution; purifying the deproteinized solution by using a hydrophilic lipophilic balance-solid phase extraction (HLB-SPE) cartridge to obtain a purified solution; subjecting the purified solution to alcohol precipitation to obtain the polysaccharide; and subjecting the polysaccharide to methylation, glycoside residue derivatization and liquid chromatography-mass spectrometry (LC-MS) analysis in sequence.

12 Claims, 8 Drawing Sheets

METHOD FOR EXTRACTING AND IDENTIFYING POLYSACCHARIDE FROM COMPLEX SAMPLE

TECHNICAL FIELD

The present disclosure relates to the technical field of extraction and identification of polysaccharide, and in particular to a method for extracting and identifying a polysaccharide form a complex sample.

BACKGROUND

Polysaccharide is a type of natural polymer composed of not less than 10 monosaccharides linked by glycosidic bonds, and is widely derived from animals, plants, algae, and microorganisms. The polysaccharide is one of the four basic substances that constitute life, and has been used in the fields such as medicine and life sciences due to desirable biological activity and low toxic side effects. Since human body lacks carbohydrate-activated enzymes (CAZymes), most polysaccharides cannot be directly digested and absorbed by the human body. However, CAZymes, encoded by the human gut microbiota, can convert oligosaccharides and polysaccharides into monosaccharides, producing easily-absorbed short-chain fatty acids and other metabolites. In addition, different types of polysaccharides can exert beneficial effects on the host by increasing beneficial intestinal microorganisms and reducing harmful intestinal microorganisms.

The biological activity of polysaccharides in vivo is affected by their digestive and glycolytic properties, and many polysaccharides are digested, fermented, and absorbed by the human body and then play a role in cells. It is helpful to explore the biological activity of the polysaccharides by comparing changes in relative molecular weight and in physical and chemical properties of reducing sugars and free monosaccharides before and after digestion and glycolysis. Therefore, it is of great significance to extract polysaccharides from feces or fermentation broth and study their structures.

The feces have a complex composition, of which ¾ is water and ¼ is solids. Among the solids, 30% are dead bacteria, 10% to 20% are fats, 2% to 3% are proteins, 10% to 20% are inorganic salts, and 30% are undigested food residues and solid components in digestive juices such as shed epithelial cells. Laboratory fermentation broth is also obtained by fermentation of fecal bacteria, and also has complex and diverse components. For the extraction of polysaccharides from complex samples such as feces or fermentation broth, traditional methods generally directly adopt ethanol precipitation or hot water extraction. The extracted crude polysaccharides contain a large number of impurities, which may cause adverse effects on subsequent analysis on structures.

SUMMARY

The present disclosure aims to provide a method for extracting a polysaccharide. The method according to the present disclosure could realize the rapid separation and purification of polysaccharides from complex samples, thereby obtaining relatively pure polysaccharides, and finally achieve accurate and quick identification of the structure of the polysaccharides.

To achieve the above object, the present disclosure provides the following technical solutions.

The present disclosure provides a method for extracting and identifying a polysaccharide from a complex sample, including the following steps:

subjecting a complex sample to be treated to sterilization and enzyme deactivation to obtain a system, and subjecting the system to solid-liquid separation to obtain a sterilization and enzyme deactivation-treated solution, the complex sample to be treated being selected from the group consisting of feces, a fermentation broth, and a medium;

deproteinizing the sterilization and enzyme deactivation-treated solution to obtain a deproteinized solution;

purifying the deproteinized solution by using a hydrophilic lipophilic balance-solid phase extraction (HLB-SPE) cartridge to obtain a purified solution;

subjecting the purified solution to alcohol precipitation to obtain the polysaccharide; and subjecting the polysaccharide to methylation, glycoside residue derivatization and liquid chromatography-mass spectrometry (LC-MS) analysis in sequence.

In some embodiments, the sterilization and enzyme deactivation is conducted at a temperature of 95° C. to 105° C. for 10 min to 20 min.

In some embodiments, under the condition that the complex sample to be treated is the feces, the sterilization and enzyme deactivation is conducted in the presence of high-temperature-resistant α-amylase.

In some embodiments, the deproteinizing is conducted 3 to 6 times by a Sevag method; and a Sevag reagent for the deproteinizing is a mixture of chloroform and n-butanol at a volume ratio of (4-5):1.

In some embodiments, the purifying is conducted by a process comprising: loading the deproteinized solution onto the HLB-SPE cartridge, and then conducting elution by using water; and combining a first effluent obtained by the loading and a second effluent obtained by the elution to obtain the purified solution; and a volume ratio of the deproteinized solution to the water for the elution is in a range of 5:(0.5-1.5).

In some embodiments, an alcohol reagent for the alcohol precipitation is absolute ethanol, and a volume ratio of the purified solution to the absolute ethanol is in a range of 1:(2-4).

In some embodiments, a methylation reagent for the methylation is methyl iodide; the methylation is conducted in the presence of NaOH-dimethyl sulfoxide suspension; and a ratio of the polysaccharide, the NaOH-dimethyl sulfoxide suspension and the methyl iodide is in a range of 100 ng:(100-300) μL:(50-60) μL.

In some embodiments, the methylation is conducted 4 to 5 times; and the methylation is conducted at a temperature of 15° C. to 35° C. for 70 min to 90 min each time.

In some embodiments, the glycoside residue derivatization is conducted by a process comprising subjecting a resulting product from the methylation to hydrolysis reaction and derivatization reaction in sequence; the hydrolysis reaction is conducted in the presence of a trifluoroacetic acid aqueous solution; and a derivatization reagent for the derivatization reaction is 1-phenyl-3-methyl-5-pyrazolone.

In some embodiments, the hydrolysis reaction is conducted at a temperature of 105° C. to 110° C. for 6 h to 7 h; and the derivatization reaction is conducted at a temperature of 60° C. to 65° C. for 20 min to 25 min.

The present disclosure provides a method for extracting and identifying a polysaccharide, including the following steps: subjecting a complex sample to be treated to sterilization and enzyme deactivation to obtain a system and subjecting the system to solid-liquid separation to obtain a sterilization and enzyme deactivation-treated solution, the complex sample to be treated being selected from the group consisting of feces, a fermentation broth, and a medium; deproteinizing the sterilization and enzyme deactivation-treated solution to obtain a deproteinized solution; purifying the deproteinized solution by using a hydrophilic lipophilic balance-solid phase extraction (HLB-SPE) cartridge to obtain a purified solution; subjecting the purified solution to alcohol precipitation to obtain the polysaccharide; and subjecting the polysaccharide to methylation, glycoside residue derivatization and liquid chromatography-mass spectrometry (LC-MS) analysis in sequence. The method according to the present disclosure could realize rapid separation and purification of polysaccharides from complex samples such as feces, a fermentation broth, or a medium. Specifically, the sterilization and enzyme deactivation as well as the solid-liquid separation could remove some insoluble impurities (such as microbial residues or insoluble proteins); the deproteinizing, the purifying by the HLB-SPE cartridge, and the alcohol precipitation could contribute to obtain relatively pure polysaccharides. Moreover, the above procedures have basically no impact on a total saccharide content, a molecular weight, and monosaccharide compositions. Further, the structure of polysaccharides could be identified accurately and rapidly by LC-MS in MRM mode combined with methylation and glycoside residue derivatization.

DETAILED DESCRIPTION

Figure 1:
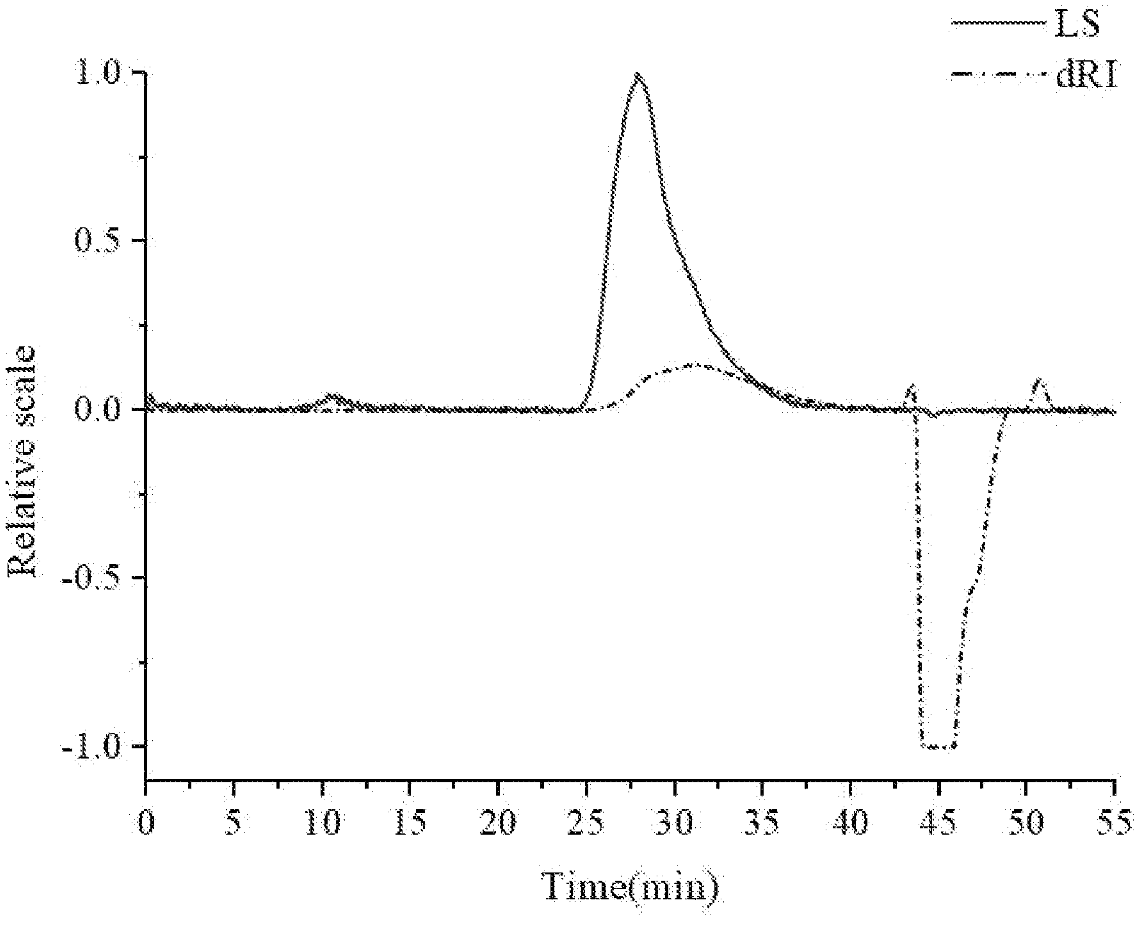
FIG. 1 shows molecular weight distribution of citrus pectin before treatment in Example 1.

The present disclosure provides a method for extracting and identifying a polysaccharide, including the following steps:

- subjecting a complex sample to be treated to sterilization and enzyme deactivation to obtain a system, and subjecting the system to solid-liquid separation to obtain a sterilization and enzyme deactivation-treated solution, the complex sample to be treated being selected from the group consisting of feces, a fermentation broth, and a medium;
- deproteinizing the sterilization and enzyme deactivation-treated solution to obtain a deproteinized solution;
- purifying the deproteinized solution by using a hydrophilic lipophilic balance-solid phase extraction (HLB-SPE) cartridge to obtain a purified solution;
- subjecting the purified solution to alcohol precipitation to obtain the polysaccharide; and
- subjecting the polysaccharide to methylation, glycoside residue derivatization and liquid chromatography-mass spectrometry (LC-MS) analysis in sequence In the present disclosure, unless otherwise specified, all raw materials used herein are commercially available products well-known to persons skilled in the art.

In some embodiments of the present disclosure, a complex sample to be treated is subjected to sterilization and enzyme deactivation to obtain a system, and the system is then subjected to solid-liquid separation to obtain a sterilization and enzyme deactivation-treated solution. In some embodiments, the complex sample to be treated is selected from the group consisting of feces, a fermentation broth, and a medium. In further embodiments, the sample to be treated is the feces or the fermentation broth. In some embodiments, mouse feces and a feces fermentation broth of pectin derived from mulberry bark (PMB) of citrus unshiu Marcovitch are used as examples for explanation. In some embodiments, the complex sample to be treated is stored in a refrigerator at −80° C. for later use. In some embodiments, the complex sample to be treated is feces, the feces is mixed with water to obtain a mixed liquid and the mixed liquid is subjected to homogenization, and then a resulting mixture is subjected to sterilization and enzyme deactivation. In some embodiments, a ratio of the feces to water is 200 mg:(800-1500) μL, preferably 200 mg:1200 μL. In some embodiments, the homogenization is conducted for 0.5 min to 1.5 min, preferably 1 min. In some embodiments, the homogenization is conducted in the presence of steel balls, which are helpful to ensure that the feces and water are evenly mixed and fully homogenized.

In some embodiments, the sterilization and enzyme deactivation is conducted at a temperature of 95° C. to 105° C., preferably 100° C. In some embodiments, the sterilization and enzyme deactivation is conducted for 10 min to 20 min, preferably 15 min. In some embodiments, the complex sample to be treated is feces, and the sterilization and enzyme deactivation is conducted in the presence of high-temperature-resistant α-amylase, and the high-temperature-resistant α-amylase is purchased from Aladdin Scientific Corp. In some embodiments, a ratio of the high-temperature-resistant α-amylase to the feces is (0.3-0.6) mL: 200 mg, preferably 0.5 mL:200 mg. Taking the mouse feces as an example: the mouse feed contains a large amount of carbohydrates such as corn starch, such that there may also be starch residues in the feces. In some embodiments, the high-temperature-resistant α-amylase is added during the sterilization and enzyme deactivation to remove residual starch in the feces. This facilitates subsequent experiment procedures and ensures the accuracy of experimental results.

In some embodiments, the solid-liquid separation is conducted by centrifugation; the centrifugation is conducted 2 to 4 times, more preferably 3 times. In some embodiments, the centrifugation is conducted at a speed of 6,000 rpm to 10,000 rpm, preferably 8,000 rpm. In some embodiments, the centrifugation is conducted for 5 min to 20 min each time, preferably 10 min. After the centrifugation is completed, a supernatant is collected as the sterilization and enzyme deactivation-treated solution.

In the present disclosure, the sterilization and enzyme deactivation-treated solution is deproteinized to obtain a deproteinized solution. In some embodiments, the deproteinizing is conducted by a Sevag method, and the deproteinizing is conducted 3 to 6 times, preferably 5 times. In some embodiments, A Sevag reagent for the deproteinizing is a mixture of chloroform and n-butanol, and a volume ratio of chloroform to n-butanol is (3-5):1, preferably 4:1. In some embodiments, the sterilization and enzyme deactivation-treated solution is mixed with the Sevag reagent, shaken and centrifuged in sequence, and a resulting middle layer of protein and a resulting lower layer of organic phase are discarded; a resulting upper layer solution is added with the Sevag reagent at the same ratio as the ratio of the sterilization and enzyme deactivation-treated solution to the Sevag reagent, and shaken and centrifuged again until no white precipitate precipitates; and a resulting supernatant is collected as the deproteinized solution. In some embodiments, a volume ratio of the sterilization and enzyme deactivation-treated solution to the Sevag reagent is in a range of 1:(3-6), preferably 1:(3-4). In some embodiments, the shaking is conducted for 0.5 min to 1.5 min, preferably 1 min. In some embodiments, the centrifugation is conducted at a speed of 4,000 rpm to 8,000 rpm, preferably 6,000 rpm; and the centrifugation is conducted for 5 min to 20 min each time, preferably 10 min. In some embodiments, the Sevag method for deproteinizing could effectively remove free proteins in the sterilization and enzyme deactivation-treated solution, and has simple operation, mild conditions, less damage to sugar chains, and cheap reagents.

In the present disclosure, the deproteinized solution is purified by using an HLB-SPE cartridge to obtain a purified solution. In some embodiments, the HLB-SPE cartridge has a volume of 3 mL; and the HLB-SPE cartridge is purchased from Huapu Biotechnology (Chongqing) Co., Ltd. In some embodiments, the HLB-SPE cartridge is subjected to activation before use, and the activation is conducted by a process including subjecting the HLB-SPE cartridge to elution treatment by using methanol and water in sequence. In some embodiments, the methanol is pure methanol, and the methanol is used at an amount of 4 mL to 6 mL, preferably 5 mL; the water is purified water, and the water is used at an amount of 8 mL to 12 mL, preferably 10 mL. In some embodiments, the purifying is conducted by a process including: loading the deproteinized solution onto the HLB-SPE cartridge, and then conducting elution with water, and combining a first effluent obtained by the loading and a second effluent obtained by the elution to obtain the purified solution. In some embodiments, a volume ratio of the deproteinized solution to the water for the elution is in a range of 5:(0.5-1.5), preferably 5:1. The HLB-SPE cartridge could purify the deproteinized solution to remove small molecule impurities (such as salts and peptides) and pigments. The HLB-SPE cartridge uses a HLB packing, which has a desirable recovery rate for non-polar to moderately-polar acidic, neutral, and alkaline compounds, and is suitable for treating complex samples such as feces, a fermentation broth, or a medium. Moreover, the HLB packing has high water wettability, is insensitive to solvent being drained, and is not easy to penetrate; it has a high recovery rate and desirable reproducibility; its adsorption capacity and sample loading capacity are much higher than that of C18 bonded silica gel (3 to 10 times); it has a tolerable pH range of 1 to 14 and is compatible with most solvents.

In the present disclosure, the purified solution is subjected to alcohol precipitation to obtain the polysaccharide. In some embodiments, an alcohol reagent for the alcohol precipitation is absolute ethanol, and a volume ratio of the purified solution to the absolute ethanol is in a rage of 1:(2-4), preferably 1:(2-3). In some embodiments, the alcohol precipitation is conducted at a temperature of 4° C. to 20° C., preferably 4° C. to 6° C. In some embodiments, the alcohol precipitation is conducted for 8 h to 24 h, preferably 12 h. After the alcohol precipitation is completed, a resulting material is subjected to the solid-liquid separation, and a resulting solid material is the polysaccharide. In some embodiments, the solid-liquid separation is conducted by centrifugation; the centrifugation is conducted at a speed of 8,000 rpm to 12,000 rpm, preferably 10,000 rpm; and the centrifugation is conducted for 15 min to 20 min, preferably 20 min. After the centrifugation is completed, a resulting supernatant is discarded, and a resulting precipitate is collected as the polysaccharide.

After the polysaccharide is obtained, the polysaccharide is subjected to methylation, glycoside residue derivatization and liquid chromatography-mass spectrometry (LC-MS) analysis in sequence. Details will be stated below.

In the present disclosure, the polysaccharide is subjected to methylation. In some embodiments, a methylation reagent for the methylation is methyl iodide. In some embodiments, the methylation is conducted in the presence of NaOH-dimethyl sulfoxide suspension. In some embodiments, a ratio of the polysaccharide, the NaOH-dimethyl sulfoxide suspension and the methyl iodide is in a range of 100 ng:(100-300) μL:(50-60) μL, preferably, 100 ng:(100-200) μL:(50-55) μL. There is no specific limitation on the method for preparing NaOH-dimethyl sulfoxide suspension, and a preparation method well-known to those skilled in the art may be used. In some embodiments, the NaOH-dimethyl sulfoxide suspension is prepared from a 50 wt % of a NaOH solution and dimethyl sulfoxide at a volume ratio of 1:20 by a method well-known to those skilled in the art. In some embodiments, the polysaccharide is dissolved in dimethyl sulfoxide to obtain a polysaccharide solution; the polysaccharide solution and the NaOH-dimethyl sulfoxide suspension are mixed at room temperature by oscillating for 35 min to 40 min to obtain a polysaccharide suspension; and the polysaccharide suspension is mixed with methyl iodide and subjected to methylation. In some embodiments, the polysaccharide solution has a concentration of 3~5 mg/mL, preferably 4 mg/mL. In some embodiments, the methylation is conducted 4 to 5 times; the methylation is conducted at a temperature of 15° C. to 35° C. each time, preferably room temperature; and the methylation is conducted for 70 min to 90 min each time, preferably 80 min to 90 min. In some embodiments, after the methylation is completed, a methylation-substituted polysaccharide product system is obtained; the methylation-substituted polysaccharide product system is then placed in an ice bath, and ice-cold water is added into the methylation-substituted polysaccharide product system until the methyl iodide therein is in an insoluble state (i.e., the system is in a turbid state); a resulting system is left to stand for 5-10 min, and then taken out from the ice bath to obtain a methylation-substituted polysaccharide liquid; the methylation-substituted polysaccharide liquid is mixed with dichloromethane, and extracted for 20 s to 30 s under a oscillating condition; a resulting upper aqueous layer is removed, and a resulting organic layer is collected and repeated the above operations 3 to 4 times to fully remove dimethyl sulfoxide, obtaining a final organic layer, where the above operations refer to steps of adding ice-cold water, standing, mixing with dichloromethane and extracting; and the final organic layer is dried by nitrogen to obtain a methylated glycoside residue.

After the methylated glycoside residue is obtained, it is subjected to glycoside residue derivatization. In some embodiments, the glycoside residue derivatization is conducted by a process including subjecting the methylated glycoside residue to hydrolysis reaction and derivatization reaction in sequence. In some embodiments, the hydrolysis reaction is conducted in the presence of a trifluoroacetic acid aqueous solution; and the trifluoroacetic acid aqueous solution has a concentration of 1.8 mol/L to 2.2 mol/L, preferably 2 mol/L. In some embodiments, the hydrolysis reaction is conducted at a temperature of 105° C. to 110° C. for 6 h to 7 h. After the hydrolysis reaction is completed, the resulting hydrolysis product system is dried by nitrogen and a resulting product after drying is mixed with an ammonia concentrate to obtain a mixture; the mixture is mixed with a derivatization reagent and subjected to derivatization reaction. In some embodiments, the derivatization reagent for the derivatization reaction is 1-phenyl-3-methyl-5-pyrazolone (PMP). In some embodiments, the PMP is in a form of a solution of PMP in methanol, and the solution of PMP in methanol has a concentration of 0.18 mol/L to 0.22 mol/L, preferably 0.2 mol/L. In some embodiments, the ammonia concentrate is of analytically pure (AR), and a volume ratio of the ammonia concentrate to the solution of PMP in methanol is 1:1. In some embodiments, the derivatization reaction is conducted at a temperature of 60° C. to 65° C. for 20 min to 25 min. In some embodiments, after the derivatization reaction is completed, a resulting reaction system is cooled to room temperature and subjected to vacuum drying to obtain a methylated PMP-derivatization glycoside residue.

After the methylated PMP-derivatization glycoside residue is obtained, it is subjected to liquid chromatography-mass spectrometry (LC-MS) analysis. In some embodiments, the methylated PMP-derivatization glycoside residue is dissolved in a methanol aqueous solution and subjected to liquid chromatography-mass spectrometry (LC-MS) analysis, and the volume percentage of methanol in the methanol aqueous solution is in a range of 65% to 75%, preferably 70%. In some embodiments, the liquid chromatography-mass spectrometry (LC-MS) analysis is performed in an MRM mode. In some embodiments, the LC-MS analysis for the methylated PMP-derivatization glycoside residue includes monosaccharide analysis and glycosidic bond analysis. Conditions for monosaccharide analysis and glycosidic bond analysis are described in detail below.

In some embodiments, the monosaccharide analysis is conducted under the following conditions.

Monosaccharide detection and quantification are determined by a Waters ACQUITY UPLC H-Class system and a Waters Xevo TQD triple quadrupole mass spectrometer (QqQ), where the chromatographic column is Agilent ZORBAX Eclipse Plus C18 column (2.1×100 mm, 1.8 μm). Mobile phase A and mobile phase B are used as the mobile phase. The mobile phase A is an ammonium acetate-acetonitrile-water solution, a concentration of ammonium acetate in the mobile phase A is 10 mmol/L and a volume percentage of acetonitrile in the mobile phase A is 5%, and a pH value of the mobile phase A is adjusted to 8.2 by using ammonia water. The mobile phase B is an acetonitrile aqueous solution with a volume percentage of 95%. A gradient elution procedure is as follows: from 0.0 min to 7.0 min, a volume percentage of the mobile phase B increases linearly from 12% to 15%; from 7.0 min to 8.5 min, a volume percentage of the mobile phase B increases linearly from 15% to 100%; from 8.5 min to 10.0 min, a volume percentage of the mobile phase B retained 100%; and from 10.0 to 16.0 min, a volume percentage of the mobile phase B decreases linearly from 100% to 12%; a flow rate of the mobile phase is 0.3 mL/min, and a column temperature is 35° C.

In some embodiments, the glycosidic bond analysis is conducted under the following conditions.

Electrospray ionization (ESI) in a positive ion mode is adopted, in which a capillary voltage is 3.5 kV; a cone hole voltage is 40V; a degassing temperature is 500° C.; a desolvation gas flow rate is 1000 L/h; and a cone hole gas flow rate is 50 L/h. a pressure of shielding gas is 30 psi, and a pressure of collision gas is 10 psi; a pressure of atomization gas and gasification gas is 55 psi; and a collision potential is +30V.

Glycosidic bond detection and quantification are determined by a Waters ACQUITY UPLC H-Class system and a Waters Xevo TQD triple quadrupole mass spectrometer (QqQ), where the chromatographic column is Agilent ZORBAX Eclipse Plus C18 column (2.1×100 mm, 1.8 μm). Mobile phase A and mobile phase B are used as the mobile phase. The mobile phase A is an ammonium acetate-acetonitrile-water solution. A concentration of ammonium acetate in the mobile phase A is 10 mmol/L and a volume percentage of acetonitrile in the mobile phase A is 5%, and a pH value of the mobile phase A is adjusted to 8.2 by using ammonia water. The mobile phase B is an acetonitrile aqueous solution with a volume percentage of 95%. A gradient elution procedure is as follows: from 0.0 min to 20.0 min, a volume percentage of the mobile phase B increases linearly from 12% to 30%; from 20.0 min to 25.0 min, a volume percentage of the mobile phase B increases linearly from 30% to 100%; from 25.0 min to 26.0 min, a volume percentage of the mobile phase B retains 100%; from 26.0 min to 26.1 min, a volume percentage of the mobile phase B decreases linearly from 100% to 12%; and from 26.1 min to 30.0 min, a volume percentage of the mobile phase B retains 12%; a flow rate of the mobile phase is 0.3 mL/min, and a column temperature is 35° C.

The glycosidic bond in the polysaccharide according to the present disclosure is analyzed after the methylation and PMP derivatization, which could not only obtain the glycosidic bond information of neutral sugar from the subsequent LC-MS analysis, but also obtain the glycosidic bond information of acidic sugar, and the analysis result is thus more real and reliable. Mass spectrometry analysis is performed by LC-MS in MRM mode, with relatively fast analysis speed and high accuracy. Further, the methylated glycoside residue is subjected to PMP derivatization in the presence of ammonia water, which could avoid introducing metal ions that interfere with mass spectrometry detection. PMP derivatization is not only beneficial to LC separation, but also could detect PMP molecules directionally by mass spectrometry and thereby quantitatively analyze glycosidic bonds. The technical solutions of the present disclosure will be clearly and completely described below in conjunction with the examples of the present disclosure. Apparently, the described examples are merely a part rather than all of the embodiments of the present disclosure. All other embodiments obtained by those skilled in the art based on the embodiments of the present disclosure without creative efforts shall fall within the scope of the present disclosure.

Example 1

In this example, a protein (specifically bovine serum albumin) was added to a polysaccharide sample to verify the effectiveness of the method according to the present disclosure as follows.

(1) Citrus pectin (purchased from Sigma-Aldrich) was mixed with water to obtain 20 mL of a citrus pectin solution with a concentration of 1 mg/mL. The protein content in the citrus pectin solution was measured by a BradFord kit, the total saccharide content in the citrus pectin solution was measured by a phenol sulfuric acid method, the molecular weight of the citrus pectin was measured by GPC, and the monosaccharide content in the citrus pectin was measured by LC-MS in MRM mode.

(2) 222 μL of bovine serum albumin was added to 10 mL of the citrus pectin solution to obtain a citrus pectin-bovine serum albumin mixed solution, where the bovine serum albumin in the citrus pectin-bovine serum albumin mixed solution had a content of 10 wt %.

(3) 5 mL of the citrus pectin-bovine serum albumin mixed solution was added in a centrifuge tube, and then transferred to a boiling water bath. 0.5 mL of high-temperature-resistant α-amylase was added (purchased from Aladdin Scientific Corp.) thereto, and a resulting mixture was heated at 100° C. for 15 min, then taken out from the boiling water bath and centrifuged twice at 8,000 rpm for 10 min each time. A resulting supernatant was collected and denoted as a first supernatant.

(4) A Sevag reagent (prepared by mixing chloroform and n-butanol at a volume ratio of 4:1) and the first supernatant were mixed in a test tube at a volume ratio of 3:1, shaken for 1 min, and then centrifuged at 6,000 rpm for 10 min. A resulting protein in the middle layer and a resulting organic phase in the lower layer were discarded, and a resulting solution in the upper layer was added with the Sevag reagent at a volume ratio of the Sevag reagent: the resulting solution of 3:1 to obtain a mixture. After that, the mixture was shaken and centrifugated 4 times until no white precipitate precipitated, and a resulting supernatant was collected and denoted as a second supernatant.

(5) An HLB-SPE cartridge (with a capacity of 3 mL, purchased from Huapu Biotechnology (Chongqing) Co., Ltd.) was subjected to activation as follows: the HLB-SPE cartridge was subjected to elution treatment by using 5 mL of pure methanol and 10 mL of pure water in sequence. After the activation was completed, the second supernatant was quantitatively loaded onto the activated HLB-SPE cartridge, and then the HLB-SPE cartridge loading the second supernatant was subjected to elution with 1 mL of pure water; the effluents from loading the second supernatant and the effluents from the subsequent elution were combined to obtain a purified solution.

(6) The purified solution and the absolute ethanol were mixed at a volume ratio of 1:2, and then centrifuged at 10,000 rpm for 20 min. A resulting supernatant was discarded, and a resulting precipitate was collected (as polysaccharide). The collected precipitate was redissolving by adding 5 mL of purified water thereto, and then a protein content, a total saccharide content, a molecular weight, and monosaccharide compositions were tested by the method in step (1).

Example 2

This example was conducted similar to Example 1, except that the citrus pectin was replaced with arabinan (purchased from Magazine).

Table 1 shows the test results of the protein content of citrus pectin and arabinan before and after being treated by the method according to the present disclosure. The results indicate that the protein content of citrus pectin and arabinan before treatment is basically negligible; after adding 10 wt % bovine serum albumins, the protein contents in the mixed solution was 0.2659±0.0197 (mg/mL) and 0.1819±0.0312 (mg/mL), respectively. After treatment by the method according to the present disclosure, the protein content in citrus pectin is no longer detectable, and there is still a trace amount of protein residue in arabinan, which could be ignored. This proves that the method according to the present disclosure is extremely effective in removing proteins from complex matrices.

TABLE 1

Test results of protein contents of citrus pectin and arabinan before and after treatment

| | Protein content (mg/mL) | | |
|---|---|---|---|
| Samples | Before treatment | After adding protein | After treatment |
| Citrus pectin | 0.0276 ± 0.0303 | 0.2659 ± 0.0197 | nd |
| Arabinan | nd | 0.1819 ± 0.0312 | 0.019 ± 0.0204 |

Table 2 shows the test results of the total saccharide contents of citrus pectin and arabinan before and after being treated by the method according to the present disclosure. The results indicate that the total saccharide contents of citrus pectin and arabinan change after being treated by the method according to the present disclosure: the total saccharide content of citrus pectin reduces by 19.6%, and the total saccharide content of arabinan reduces by 9.4%. This is because a small amount of sample volume is lost during the deproteinizing and alcohol precipitation steps, resulting in changes in the total saccharide contents of citrus pectin and arabinan, which are still within an acceptable range.

TABLE 2

Test results of total saccharide contents of citrus pectin and arabinan before and after treatment

| | Total saccharide content (mg/mL) | |
|---|---|---|
| Samples | Before treatment | After treatment |
| Citrus pectin | 1.17 ± 0.10 | 0.94 ± 0.04 |
| Arabinan | 1.76 ± 0.04 | 1.60 ± 0.03 |

Figure 2:
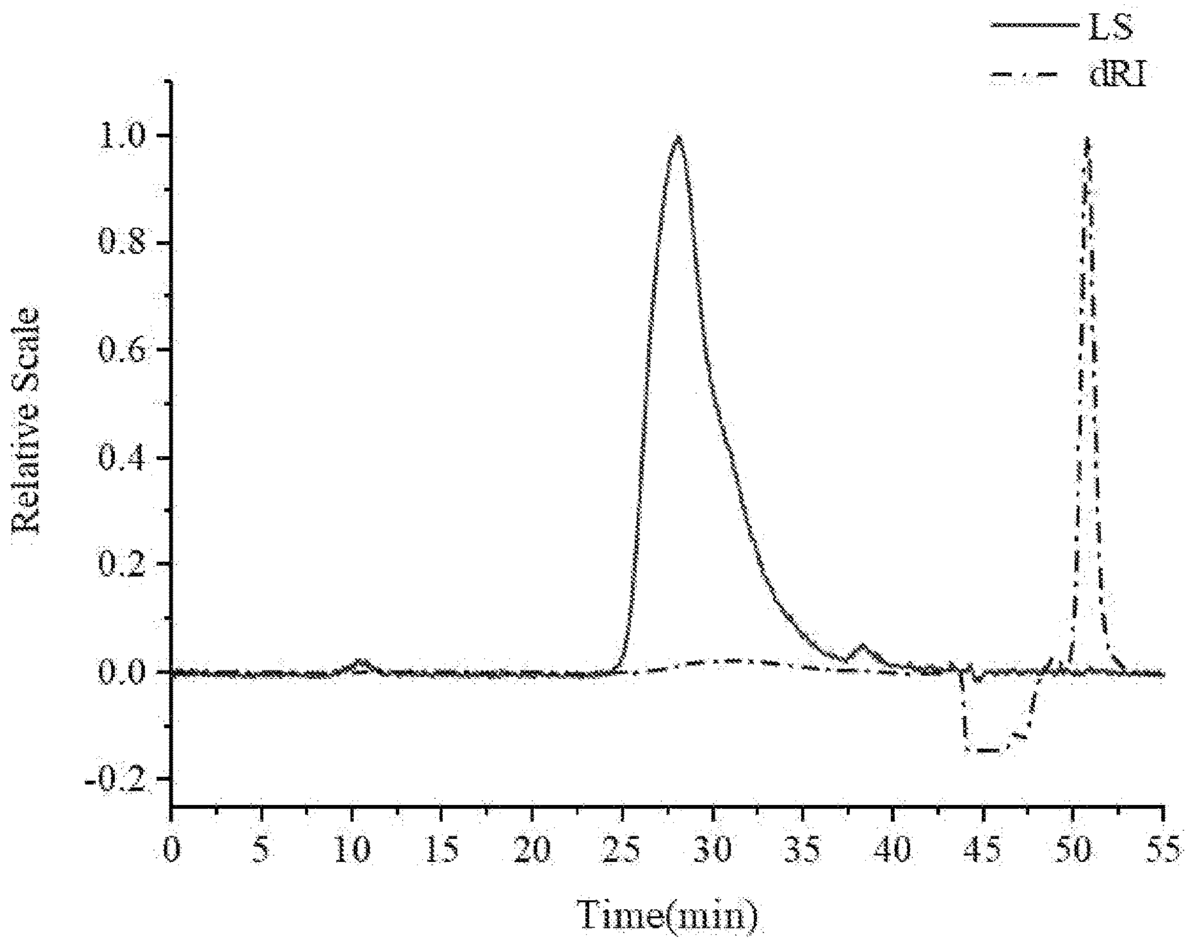
FIG. 2 shows molecular weight distribution of citrus pectin after treatment in Example 1.
Figure 3:
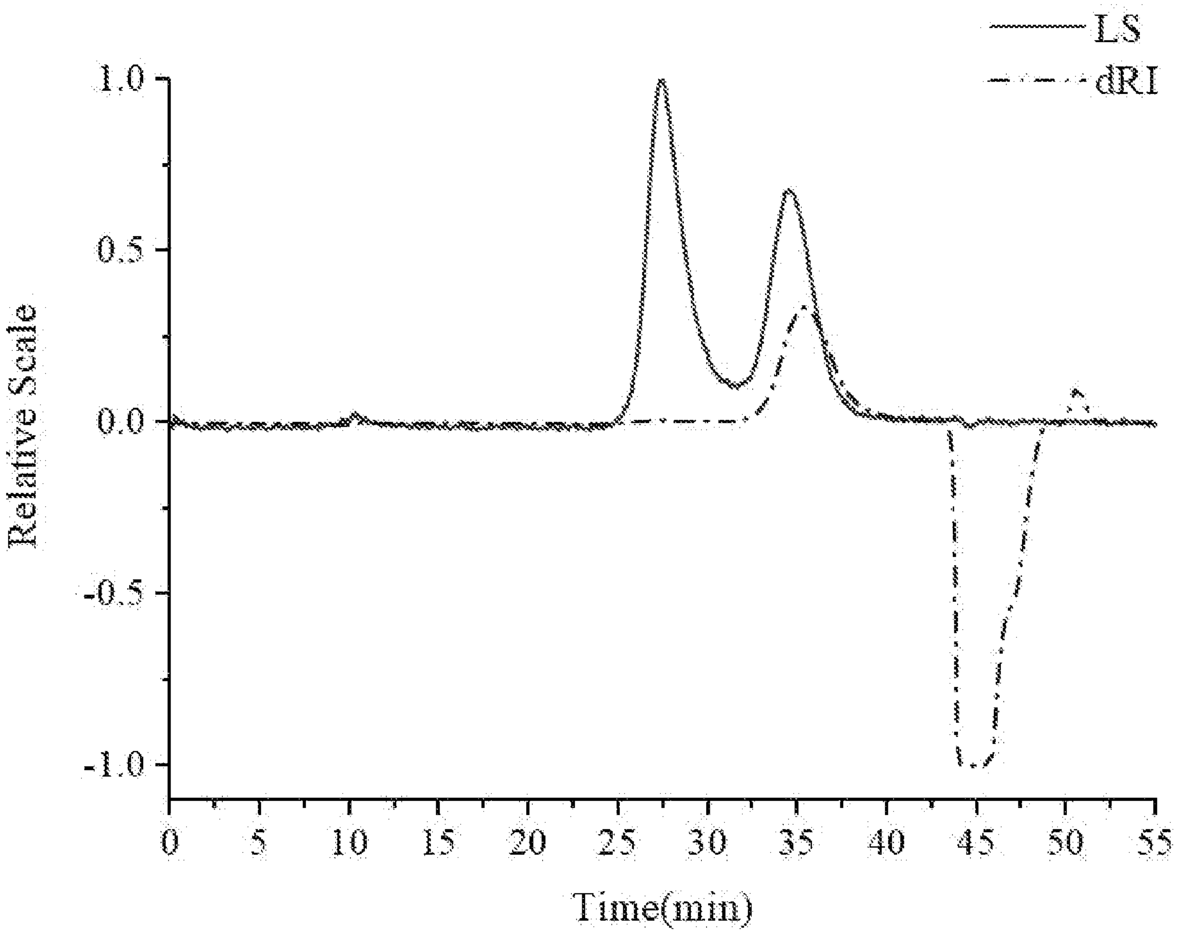
FIG. 3 shows molecular weight distribution of arabinan before treatment in Example 2.
Figure 4:
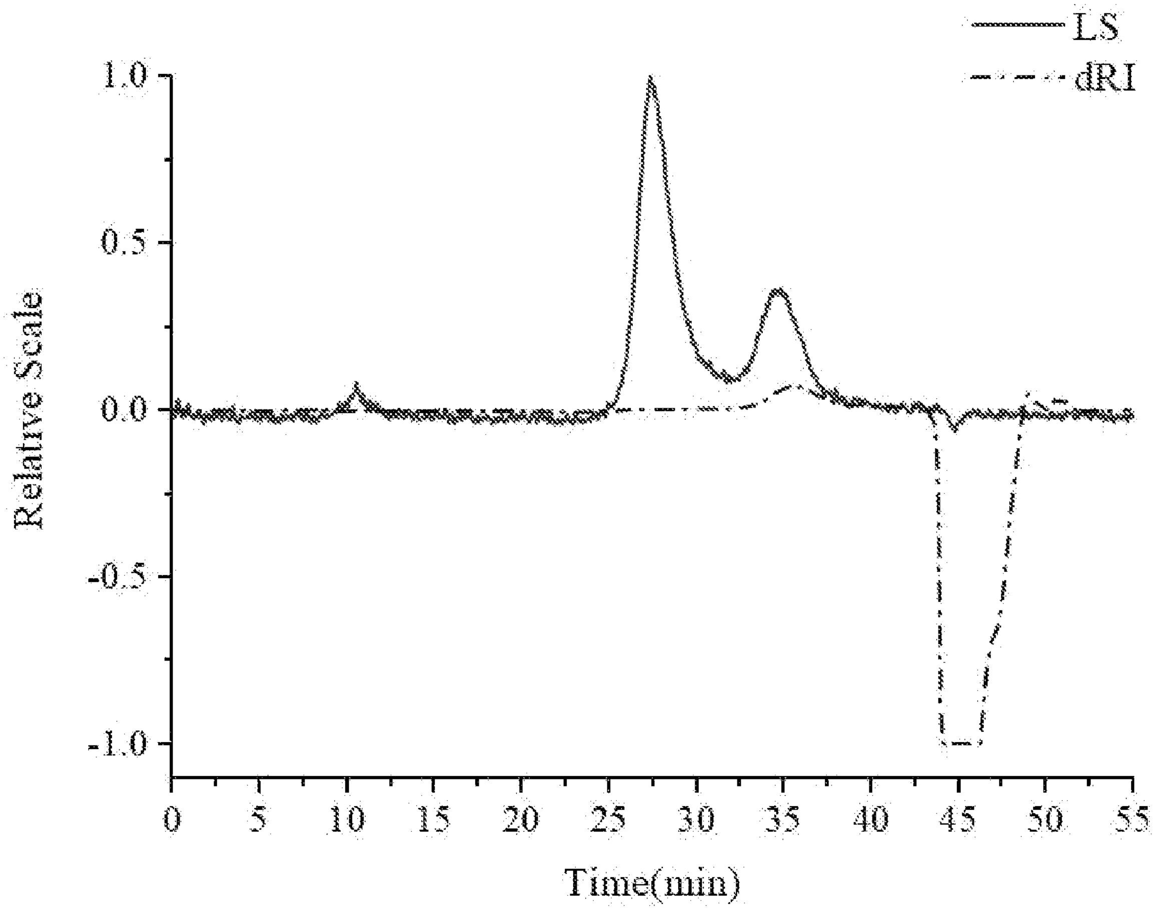
FIG. 4 shows molecular weight distribution of arabinan after treatment in Example 2.

FIG. 1 shows molecular weight distribution of citrus pectin before treatment in Example 1; FIG. 2 shows molecular weight distribution of citrus pectin after treatment in Example 1; FIG. 3 shows molecular weight distribution of arabinan before treatment in Example 2; and FIG. 4 shows molecular weight distribution of arabinan after treatment in Example 2. Table 3 shows the test results of molecular weights of citrus pectin and arabinan before and after being treated by the method according to the present disclosure. As shown in FIG. 1 to FIG. 4 and Table 3, there is basically no change in the molecular weights of citrus pectin and arabinan before and after being treated by the method according to the present disclosure, indicating that the method according to the present disclosure basically does not change the molecular weight of complex matrix samples.

TABLE 3

Test results of molecular weights of citrus pectin and arabinan before and after treatment

| | Molecular weight (Mw) g/mol | |
|---|---|---|
| Samples | Before treatment | After treatment |
| Citrus pectin | $2.264 \times 10^5$(±3.053%) | $2.012 \times 10^5$(±5.254%) |
| Arabinan | $6.367 \times 10^4$(±1.729%) | $6.490 \times 10^4$(±8.636%) |

Figure 5:
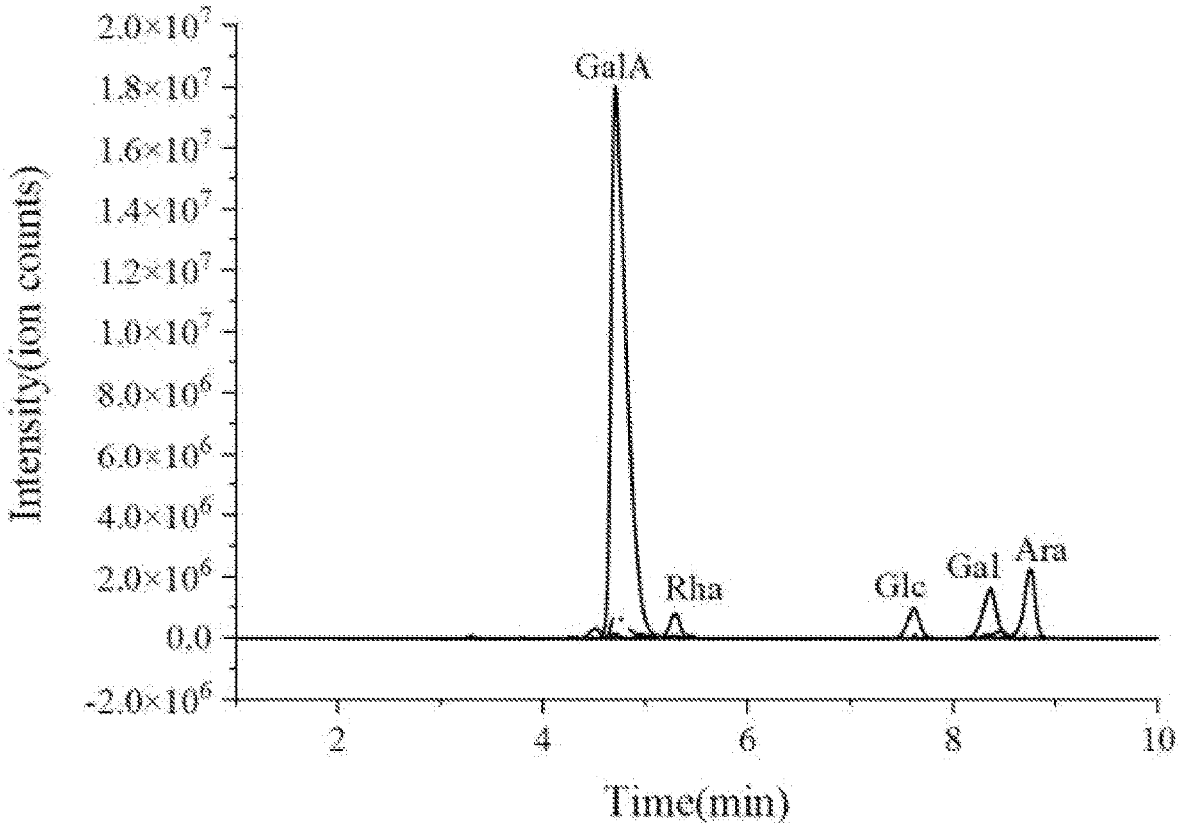
FIG. 5 shows a multiple reaction monitoring (MRM) chromatogram of monosaccharide compositions of citrus pectin before treatment in Example 1.
Figure 6:
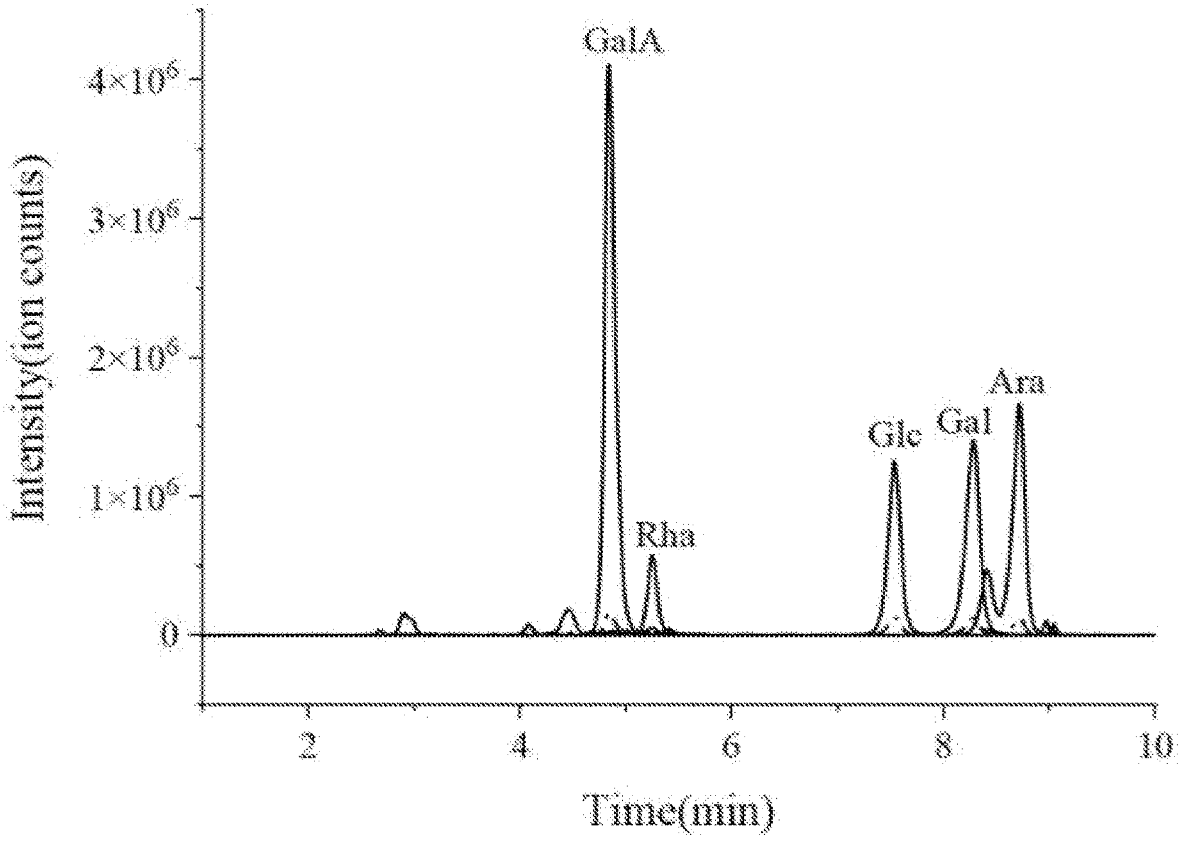
FIG. 6 shows an MRM chromatogram of monosaccharide compositions of citrus pectin after treatment in Example 1.
Figure 7:
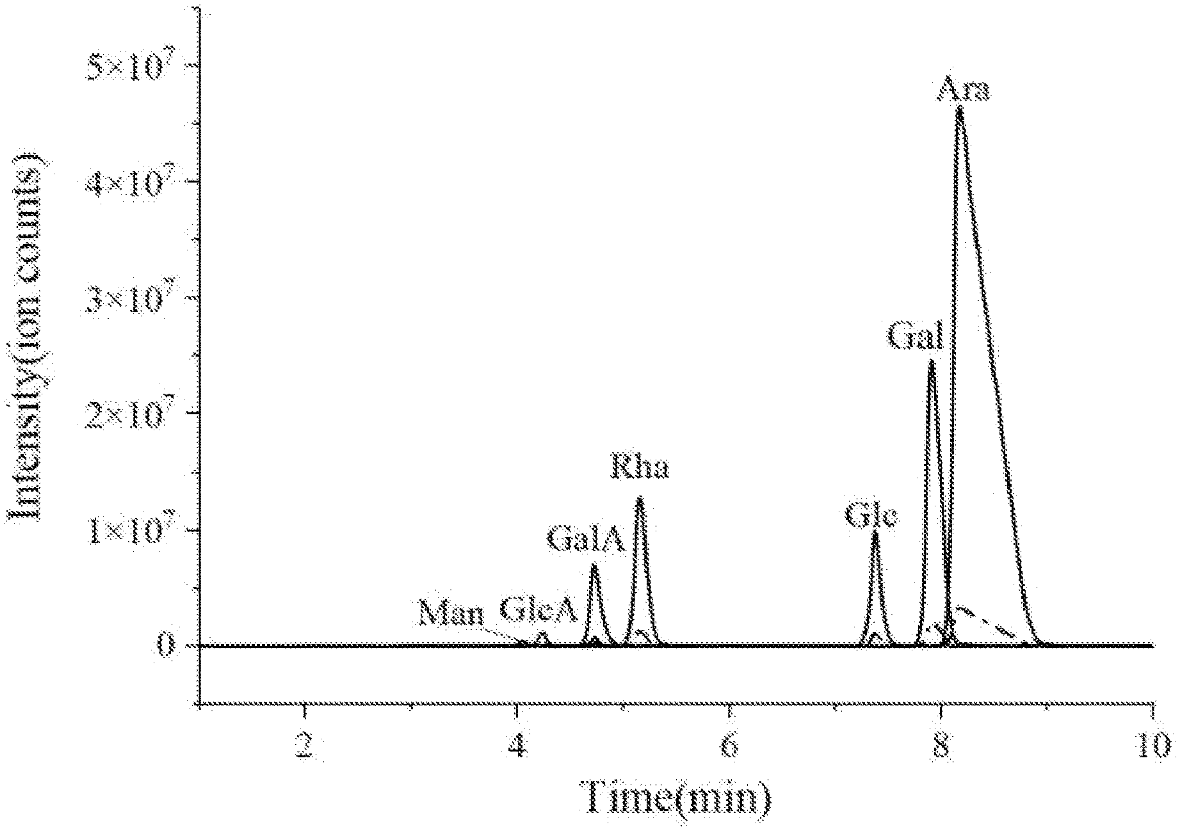
FIG. 7 shows an MRM chromatogram of monosaccharide compositions of arabinan before treatment in Example 2.
Figure 8:
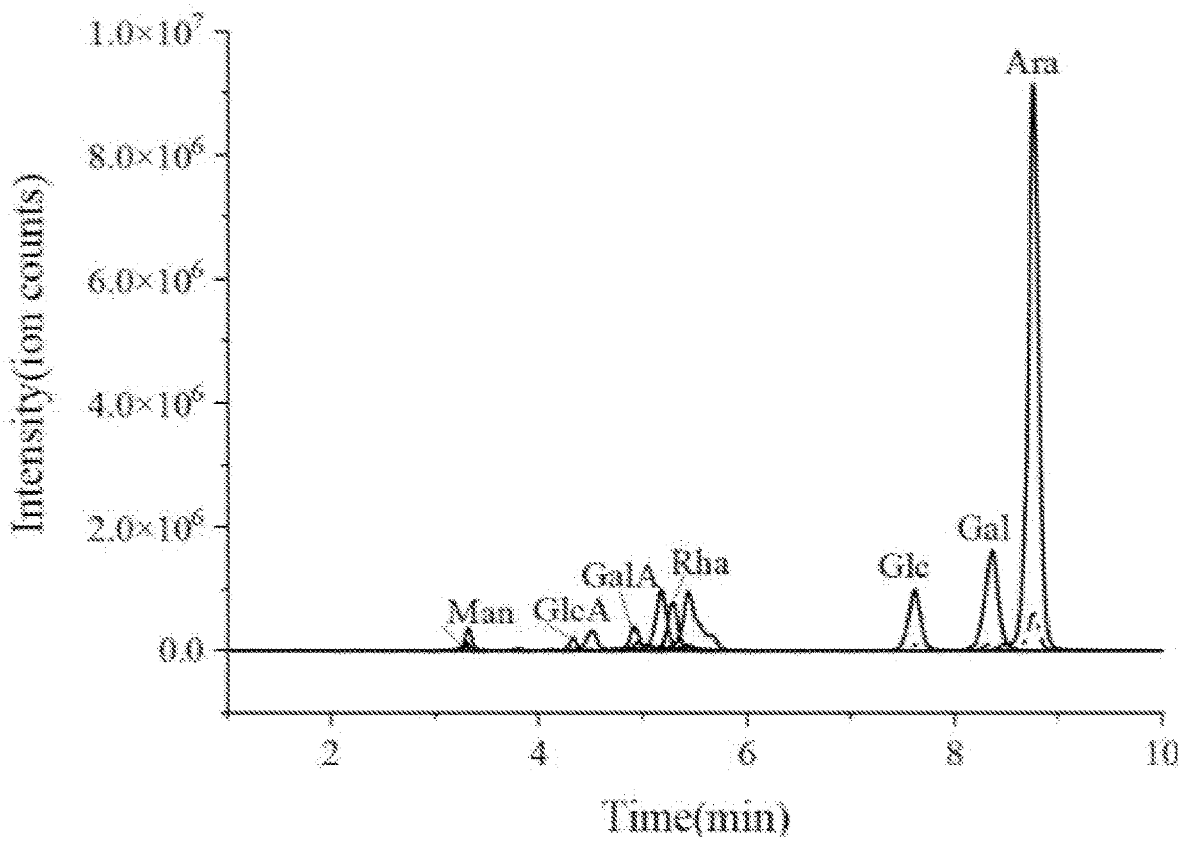
FIG. 8 shows an MRM chromatogram of monosaccharide compositions of arabinan after treatment in Example 2.

FIG. 5 shows an MRM chromatogram of a monosaccharide composition of citrus pectin before treatment in Example 1; FIG. 6 shows an MRM chromatogram of a monosaccharide composition of citrus pectin after treatment in Example 1; FIG. 7 shows an MRM chromatogram of monosaccharide compositions of arabinan before treatment in Example 2; and FIG. 8 shows an MRM chromatogram of monosaccharide compositions of arabinan before treatment in Example 2. Table 4 shows the test results of monosaccharide compositions of citrus pectin and arabinan before and after being treated by the method according to the present disclosure. As shown in FIG. 5 to FIG. 8 and Table 4, there is basically no change in the monosaccharide compositions of citrus pectin and arabinan before and after be treated by the method according to the present disclosure indicating that the method according to the present disclosure does not basically change the monosaccharide compositions of complex matrix samples.

phase in the lower layer were discarded, and a resulting solution in the upper layer was added with a Sevag reagent at a volume ration of the Sevag reagent: the resulting solution of 3:1 to obtain a mixture. After that, the mixture was shaken and centrifugated 4 times until no white precipitate precipitated, and a resulting supernatant was collected and denoted as a second supernatant.

An HLB-SPE cartridge (with a capacity of 3 mL) was subjected to activation as follows: the HLB-SPE cartridge was subjected to elution treatment by using 5 mL of pure methanol and 10 mL of pure water in sequence. After the activation was completed, the second supernatant was quantitatively loaded onto the activated HLB-SPE cartridge, and then the HLB-SPE cartridge loading the second supernatant was subjected to elution with 1 mL of pure water; the effluents from loading the second supernatant and the effluents from the subsequent elution were combined to obtain a purified solution.

TABLE 4

Test results of monosaccharide compositions of citrus pectin and arabinan before and after treatment

| Monosaccharide type | Monosaccharide compositions in sample (mol %) Citrus pectin Before treatment | Citrus pectin After treatment | Arabinan Before treatment | Arabinan After treatment |
|---|---|---|---|---|
| GlcA | 0 | 0 | 0.86 | 0.63 ± 0.10 |
| GalA | 74.83 ± 3.59 | 70.2 ± 1.09 | 6.06 | 4.60 ± 0.37 |
| Man | 0.66 ± 0.89 | 0.15 ± 0.01 | 0.23 | 0.37 ± 0.02 |
| Glc | 9.74 ± 3.22 | 9.88 ± 0.43 | 6.07 | 7.14 ± 1.49 |
| Gal | 10.97 ± 1.68 | 12.33 ± 0.58 | 21.27 | 20.76 ± 2.46 |
| Xyl | 0.19 ± 0.17 | 0.42 ± 0.03 | 0 | 0 |
| Ara | 2.00 ± 1.52 | 4.01 ± 0.17 | 60.16 | 61.56 ± 1.9 |
| Rha | 1.58 ± 1.42 | 2.78 ± 0.1 | 5.34 | 4.94 ± 0.57 |
| Fuc | 0.02 ± 0.04 | 0.23 ± 0.04 | 0 | 0 |

Example 3

In this example, polysaccharides were extracted from mouse feces. A control group, a model group, and a raspberry pectin group were selected from the animal experiments in which raspberry pectin alleviated the DSS-induced mouse colitis model. Specifically, the mice in the control group and the model group were fed ordinary purified feed, while the mice in the raspberry pectin group were fed the feed added with 3 wt % raspberry pectin; the mice in the control group were not induced by DSS colitis, while the mice in the model group and the raspberry pectin group were induced by DSS colitis. The mouse feces samples at three specific times (day 0, day 8, and day 12) were selected (7 groups in total).

200 mg of the mouse feces was mixed with 1,200 μL of purified water, and a resulting mixture was added with steel beads, and homogenized for 1 min, and then transferred to a boiling water bath. 0.5 mL of high-temperature-resistant α-amylase was added thereto, and a resulting mixed system was heated at 100° C. for 15 min, taken out from the boiling water bath and centrifuged twice at 8,000 rpm for 10 min each time. A resulting supernatant was collected and denoted as a first supernatant.

A Sevag reagent (prepared by mixing chloroform and n-butanol at a volume ratio of 4:1) and the first supernatant were mixed in a test tube at a volume ratio of 3:1, shaken for 1 min, and then centrifuged at 6,000 rpm for 10 min. A resulting protein in the middle layer and a resulting organic The purified solution and the absolute ethanol were mixed at a volume ratio of 1:2, and centrifuged at 10,000 rpm for 20 min. A resulting supernatant was discarded, and a resulting precipitate was collected as polysaccharide.

The collected precipitate was redissolved by adding 5 mL of purified water thereto, and then freeze-dried to obtain a freeze-dried polysaccharide solution. The freeze-dried polysaccharide solution was dissolved in anhydrous dimethyl sulfoxide (DMSO) to prepare a polysaccharide solution with a concentration of 4 mg/mL. 100 μL of the polysaccharide solution and 100 μL of a NaOH-dimethyl sulfoxide suspension are mixed at room temperature by oscillating for 40 min to obtain a polysaccharide suspension, and the NaOH-dimethyl sulfoxide suspension are prepared from 1 mL of 50 wt % of NaOH solution and 20 mL of dimethyl sulfoxide (DMSO). 50 μL of methyl iodide was added into the polysaccharide suspension, and the resulting mixture was subjected to methylation for 1.5 h. The operation of adding methyl iodide and subjecting to methylation was repeated 4 times. After that, a methylation-substituted polysaccharide product system was obtained, and placed in an ice bath. 400 μL of ice-cold water (with a temperature of 4° C.) was then added into the methylation-substituted polysaccharide product system until the methyl iodide therein is in an insoluble state (i.e., the system is in a turbid state). A resulting system was left to stand for 10 min, and then taken out from the ice bath to obtain a methylation-substituted polysaccharide liquid; the methylation-substituted polysaccharide liquid was mixed with 500 μL of dichloromethane, and extracted for 30 s under a oscillating condition; a resulting upper aqueous layer (containing DMSO) was removed, and a resulting organic layer was collected, the above operations (i.e. adding ice-cold water, standing, mixing with dichloromethane and extracting) was repeated on the organic layer 4 times to fully remove dimethyl sulfoxide, obtaining a final organic layer. The final organic layer was dried by nitrogen to obtain a methylated glycoside residue.

The methylated glycoside residue was added with 300 μL of 2 mol/L trifluoroacetic acid aqueous solution and subjected to hydrolysis reaction at 110° C. for 6 h. After the hydrolysis reaction was completed, the resulting hydrolysis product system was dried by nitrogen. A dried product was mixed with 200 μL of ammonia concentrate (AR, analytically pure) and 200 μL of 0.2 mol/L a solution of 1-phenyl-3-methyl-5-pyrazolone (PMP) in methanol, the resulting system was then subjected to derivatization reaction in a water bath at 65° C. for 25 min. After the derivatization reaction was completed, a resulting reaction system was cooled to room temperature and subjected to vacuum drying to obtain a methylated PMP-derivatization glycoside residue.

The methylated PMP-derivatization glycoside residue was dissolved in 1 mL of methanol aqueous solution with a volume percentage of 70%, and then monosaccharide compositions and glycosidic bond compositions of the polysaccharide were detected by liquid chromatography-mass spectrometry (LC-MS) in MRM mode. Devices, conditions and parameters used herein are as follows.

The monosaccharide analysis was conducted under the following conditions. Monosaccharide detection and quantification was determined by a Waters ACQUITY UPLC H-Class system and a Waters Xevo TQD triple quadrupole mass spectrometer (QqQ), where the chromatographic column was Agilent ZORBAX Eclipse Plus C18 column (2.1×100 mm, 1.8 μm). Mobile phase A and mobile phase B were used as the mobile phase. The mobile phase A was an ammonium acetate-acetonitrile-water solution, a concentration of ammonium acetate in the mobile phase A was 10 mmol/L and a volume percentage of acetonitrile in the mobile phase A was 5%, and a pH value of the mobile phase A was adjusted to 8.2 by using ammonia water. The mobile phase B was an acetonitrile aqueous solution with a volume percentage of 95%. A gradient elution procedure was as follows: from 0.0 min to 7.0 min, a volume percentage of the mobile phase B increased linearly from 12% to 15%; from 7.0 min to 8.5 min, the volume percentage of the mobile phase B increased linearly from 15% to 100%; from 8.5 min to 10.0 min, a volume percentage of the mobile phase B retained 100%; and from 10.0 to 16.0 min, a volume percentage of the mobile phase B decreased linearly from 100% to 12%; a flow rate of the mobile phase was 0.3 mL/min, and a column temperature was 35° C.

The glycosidic bond analysis was conducted under the following conditions, Electrospray ionization (ESI) in a positive ion mode was adopted, in which a capillary voltage was 3.5 kV, a cone hole voltage was 40 V, a degassing temperature was 500° C., a desolvation gas flow rate was 1000 L/h, and a cone hole gas flow rate was 50 L/h; a pressure of shielding gas was 30 psi, and a pressure of collision gas was 10 psi; a pressure of atomization gas and gasification gas was 55 psi; and a collision potential was ±30V.

Glycosidic bond detection and quantification was determined by a Waters ACQUITY UPLC H-Class system and a Waters Xevo TQD triple quadrupole mass spectrometer (QqQ), where the chromatographic column was Agilent ZORBAX Eclipse Plus C18 column (2.1×100 mm, 1.8 μm). Mobile phase A and mobile phase B were used as the mobile phase. The mobile phase A was an ammonium acetate-acetonitrile-water solution, a concentration of ammonium acetate in the mobile phase A was 10 mmol/L and a volume percentage of acetonitrile in the mobile phase A was 5%, and a pH value of the mobile phase A was adjusted to 8.2 by using ammonia water. The mobile phase B was an acetonitrile aqueous solution with a volume percentage of 95%. A gradient elution procedure was as follows: from 0.0 min to 20.0 min, a volume percentage of the mobile phase B increased linearly from 12% to 30%; from 20.0 min to 25.0 min, a volume percentage of the mobile phase B increased linearly from 30% to 100%; from 25.0 min to 26.0 min, a volume percentage of the mobile phase B retained 100%; from 26.0 min to 26.1 min, a volume percentage of the mobile phase B decreased linearly from 100% to 12%; and from 26.1 min to 30.0 min, a volume percentage of the mobile phase B retained 12%; a flow rate of mobile phase was 0.3 mL/min, and a column temperature was 35° C.

Tables 5 to 7 shows the test results of monosaccharide compositions of the polysaccharide in the feces of mice in each group. As shown in Tables 5 to 7, both normal mice and colitis mice have the highest glucose content in their feces. This is because the feed consumed by the mice is added with about 60% carbohydrates containing a large amount of maltodextrin and corn starch. Although high-temperature-resistant α-amylase is added during the extraction, maltodextrin is a polysaccharide, such that there is about 70% glucose in mouse feces. Further, due to the addition of 3 wt % raspberry pectin to the feed, the galacturonic acid content in the feces of mice in the raspberry pectin group increases to 12%. Days 8 to 12 were a modeling period. After the mice taken feed containing raspberry pectin, they gradually began to utilize galacturonic acid. On the 12th day, the galacturonic acid content in the feces of colitis mice dropped to 5.85%, indicating that colitis mice ingest raspberry pectin in the intestines, which results in a decrease in the unused galacturonic acid content in the mouse feces. This is also consistent with a result of mouse colitis experiments that the raspberry pectin has a therapeutic effect on colitis.

TABLE 5

Test results of monosaccharide compositions of polysaccharide in feces of mice in control group

| Monosaccharide types in polysaccharide | Monosaccharide compositions of polysaccharide in feces of mice in control group (mol %) | |
|---|---|---|
| | 0 d | 8 d |
| GlcA | 0.20 ± 0.04 | 0.22 ± 0.03 |
| GalA | 0.55 ± 0.14 | 0.26 ± 0.10 |
| Man | 1.59 ± 0.23 | 1.11 ± 0.07 |
| Glc | 78.64 ± 2.06 | 78.00 ± 0.81 |
| Gal | 2.69 ± 0.07 | 2.59 ± 0.36 |
| Xyl | 10.98 ± 1.86 | 13.23 ± 1.40 |
| Ara | 2.82 ± 0.12 | 2.41 ± 0.55 |
| Rha | 1.15 ± 0.05 | 1.07 ± 0.02 |
| Fuc | 1.38 ± 0.06 | 1.11 ± 0.17 |

TABLE 6

Test results of monosaccharide compositions of polysaccharide in feces of mice in model group

| Monosaccharide types in | Monosaccharide compositions of polysaccharide in feces of mice in model group (mol %) | | |
|---|---|---|---|
| polysaccharide | 0 d | 8 d | 12 d |
| GlcA | 0.25 ± 0.01 | 0.21 ± 0.02 | 0.74 ± 0.05 |
| GalA | 0.23 ± 0.01 | 0.19 ± 0.08 | 0.39 ± 0.41 |
| Man | 1.15 ± 0.03 | 2.13 ± 0.17 | 1.32 ± 0.08 |
| Glc | 78.19 ± 0.80 | 75.37 ± 0.51 | 78.30 ± 1.53 |
| Gal | 3.72 ± 0.11 | 3.28 ± 0.71 | 5.68 ± 0.46 |
| Xyl | 11.10 ± 0.40 | 14.45 ± 0.73 | 7.32 ± 0.29 |
| Ara | 1.97 ± 0.19 | 2.09 ± 0.10 | 2.54 ± 0.31 |
| Rha | 1.30 ± 0.06 | 1.09 ± 0.09 | 1.12 ± 0.05 |
| Fuc | 2.09 ± 0.27 | 1.19 ± 0.016 | 2.59 ± 0.28 |

TABLE 7

Test results of monosaccharide compositions of polysaccharide in feces of mice in raspberry pectin group

| Monosaccharide types in | Monosaccharide compositions of polysaccharide in feces of mice in raspberry pectin group (mol %) | |
|---|---|---|
| polysaccharide | 8 d | 12 d |
| GlcA | 1.03 ± 0.10 | 0.09 ± 0.02 |
| GalA | 12.71 ± 2.58 | 5.85 ± 1.59 |
| Man | 1.50 ± 0.45 | 0.57 ± 0.07 |
| Glc | 57.37 ± 4.89 | 76.82 ± 1.66 |

TABLE 7-continued

Test results of monosaccharide compositions of polysaccharide in feces of mice in raspberry pectin group

| Monosaccharide types in | Monosaccharide compositions of polysaccharide in feces of mice in raspberry pectin group (mol %) | |
|---|---|---|
| polysaccharide | 8 d | 12 d |
| Gal | 10.43 ± 0.26 | 4.27 ± 0.23 |
| Xyl | 7.83 ± 0.86 | 6.14 ± 0.49 |
| Ara | 2.61 ± 0.46 | 3.43 ± 0.56 |
| Rha | 3.18 ± 0.37 | 1.59 ± 0.26 |
| Fuc | 3.35 ± 0.49 | 1.24 ± 0.23 |

Tables 8 to 10 show the test results of the glycosidic bond compositions of polysaccharide in the feces of mouse in each group and raspberry pectin. As shown in Tables 8 to 10, since most of the polysaccharides extracted from mouse feces are glucose, the glycosidic bond composition is basically glucose. However, it can also be seen that in the raspberry pectin group, due to the addition of raspberry pectin to the feed, the galactose and galacturonic acid contents increases, especially 1,4-GalA. In the feces of the mice in the raspberry pectin group on the eighth day, the 1,4-GalA content reaches to 3.68%. Since the mice in the raspberry pectin group were colitis mice from the 8th to the 12th days, the intestines began to gradually utilize raspberry pectin, resulting in a decrease in the 1,4-GalA content in the feces of mice in the raspberry pectin group on the 12th day. This is also consistent with the monosaccharide composition results of polysaccharide in Tables 5 to 7.

TABLE 8

Test results of glycosidic bond compositions of polysaccharide in feces of mice in control group

| Day | Glycosidic bond compositions of polysaccharide in feces of mice (mol %) | | | | | | |
|---|---|---|---|---|---|---|---|
| Control group, 0 d | 6-Glc | T-Glc | T-Gal | 4-Gal | 4-Glc | X-Rha | T-Ara |
| | 12.47% | 10.65% | 9.27% | 9.12% | 9.11% | 5.56% | 5.38% |
| | 4-Fuc | 6-Man | 6-Gal | 2,X-Gal | 2-Gal | 3-Glc | 2-Ara |
| | 4.75% | 4.22% | 4.14% | 3.29% | 3.16% | 3.13% | 3.01% |
| | 3-Fuc | 3,4-Fuc | 2,X-Xyl | 2,3-Glc | 3,6-Gal | / | / |
| | 2.04% | 1.50% | 1.50% | 1.38% | 1.30% | / | / |
| Control group, 8 d | 6-Glc | 4-Glc | 2-Gal | 3-Glc | 2-Ara | X-Rha | T-Ara |
| | 10.15% | 7.02% | 6.74% | 6.43% | 6.37% | 5.06% | 4.99% |
| | 6-Gal | X,X-Man | 2,X-Gal | 6-Man | 4-Fuc | 2-Man | 4-Gal |
| | 4.51% | 4.35% | 4.30% | 4.23% | 3.45% | 3.12% | 2.59% |
| | 2,3-Glc | 3,4-Fuc | 2,X-Xyl | 3.4-Gal | 4,6-Man | / | / |
| | 2.59% | 2.40% | 2.36% | 2.21% | 2.18% | / | / |

TABLE 9

Test results of glycosidic bond compositions of polysaccharide in feces of mice in model group

| Day | Glycosidic bond compositions of polysaccharide in feces of mice (mol %) | | | | | | |
|---|---|---|---|---|---|---|---|
| Model group, 0 d | 6-Glc | 4-Glc | T-Glc | T-Gal | 2,X-Gal | X,X-Man | 6-Man |
| | 12.75% | 11.39% | 6.72% | 6.44% | 5.81% | 5.80% | 5.04% |
| | 6-Gal | 3,4-Fuc | 2-Ara | 2-Glc | 3-Glc | X-Rha | 2-Gal |
| | 4.23% | 3.76% | 3.64% | 3.31% | 3.10% | 3.05% | 3.00% |
| | T-Ara | 3,6-Gal | 4-Gal | 2,X-Xyl | 3-Man | / | / |
| | 2.92% | 2.87% | 2.69% | 1.73% | 1.57% | / | / |
| Model group, 8 d | 6-Glc | 3,6-Gal | 2,3-Glc | 4-Glc | 3-Glc | 3,4-Fuc | 2,4-Gal |
| | 10.46% | 8.63% | 8.41% | 6.25% | 6.25% | 5.79% | 5.66% |
| | 2-Ara | 4-Gal | X,X-Man | 6-Man | 6-Gal | X-Rha | T-Ara |
| | 5.35% | 4.90% | 4.85% | 4.67% | 4.64% | 3.00% | 2.90% |
| | 2-Gal | 2,4,6-Glc | X,X-Gal | 2,X,X-Glc | T-Glc | / | / |
| | 2.86% | 2.44% | 2.42% | 2.06% | 1.48% | / | / |

TABLE 9-continued

| Test results of glycosidic bond compositions of polysaccharide in feces of mice in model group | | | | | | | |
|---|---|---|---|---|---|---|---|
| Day | Glycosidic bond compositions of polysaccharide in feces of mice (mol %) | | | | | | |
| Model | 6-Glc | 4-Glc | 4-Gal | 2,3-Glc | 3.6-Gal | 6-Gal | 4-Man |
| group, 12 d | 6.74% | 5.40% | 5.33% | 5.28% | 5.16% | 4.20% | 4.04% |
| | 3,4-Fuc | 2-Ara | 2,X-Gal | T-Glc | X,X-Man | 2,X-Glc | 4,6-Gal |
| | 3.84% | 3.81% | 3.27% | 3.07% | 3.03% | 2.99% | 2.99% |
| | 2-Gal | T-Ara | X-Rha | 3-Man | 6-Man | / | / |
| | 2.87% | 2.74% | 2.66% | 2.63% | 2.52% | / | / |

TABLE 10

| Test results of glycosidic bond composition of polysaccharide in feces of mice in raspberry pectin group and raspberry pectin | | | | | | | |
|---|---|---|---|---|---|---|---|
| Day | Glycosidic bond composition of polysaccharide in feces of mice and raspberry pectin (mol %) | | | | | | |
| Raspberry pectin | 6-Glc | 4-Glc | 3,6-Gal | 4-Gal | 3-Glc | 6-Gal | X-Rha |
| group, 8 d | 6.38% | 5.36% | 5.28% | 5.27% | 4.59% | 4.50% | 4.14% |
| | 4-Fuc | T-Ara | 4-GalA | 2-Ara | T-Glc | T-Gal | 6-Man |
| | 4.11% | 4.09% | 3.68% | 3.50% | 3.38% | 3.32% | 3.29% |
| | 3-Man | 2,X-Gal | 3-Gal | 3-Fuc | 3,4-Fuc | / | / |
| | 3.13% | 2.99% | 2.55% | 2.37% | 2.35% | / | / |
| | 6-Glc | 4-Glc | 3,6-Gal | 3-Glc | 3-Gal | 3-Man | 2,3-Glc |
| Raspberry pectin | 8.40% | 6.35% | 6.12% | 5.62% | 5.20% | 5.19% | 5.11% |
| group, 12 d | 2-Ara | 4-Gal | 3,4-Fuc | T-Glc | 2,X-Gal | T-Gal | 2-Gal |
| | 4.97% | 4.04% | 3.29% | 3.15% | 2.97% | 2.95% | 2.51% |
| | 6-Man | X-Rha | T-Ara | 2-Glc | 4-GalA | / | / |
| | 2.50% | 2.48% | 2.45% | 1.89% | 1.87% | / | / |
| | 6-Glc | 6-Gal | T-Ara | 4-Glc | 4-Fuc | 2-Ara | 4-GalA |
| Raspberry pectin | 10.12% | 9.93% | 7.52% | 5.61% | 5.12% | 5.04% | 4.63% |
| | 6-Man | X-Rha | 2,X-Gal | 2,3-Glc | 3,6-Gal | 2,X-Glc | 2-Fuc |
| | 3.60% | 3.59% | 3.32% | 3.31% | 3.23% | 3.03% | 2.75% |
| | 3-Man | 3,4-Fuc | 4,6-Man | 2-Glc | 2-Xyl | / | / |
| | 2.30% | 2.28% | 2.10% | 1.90% | 1.86% | / | / |

Example 4

In this example, the polysaccharide in a fermentation broth was extracted as follows:

The fermentation broth was transferred to a boiling water bath, heated at 100° C. for 15 min, taken out from the boiling water bath and centrifuged twice at 8,000 rpm for 10 min each time. A resulting supernatant was collected and denoted as a first supernatant.

A Sevag reagent (prepared by mixing chloroform and n-butanol at a volume ratio of 4:1) and the first supernatant were mixed in a test tube at a volume ratio of 3:1, shaken for 1 min, and then centrifuged at 6,000 rpm for 10 min. A resulting protein in the middle layer and a resulting organic phase in the lower layer were discarded, and a resulting solution in the upper layer was added with the Sevag reagent at a volume ration of Sevag reagent: the resulting solution of 3:1 to obtain a mixture. After that the mixture was shaken and centrifugated 4 times until no white precipitate precipitated, and a resulting supernatant was collected and denoted as a second supernatant.

An HLB-SPE cartridge (with a capacity of 3 mL) was subjected to activation as follows: the HLB-SPE cartridge was subjected to elution treatment by using 5 mL of pure methanol and 10 mL of pure water in sequence. After the activation was completed, the second supernatant was quantitatively loaded onto the activated HLB-SPE cartridge, and then the HLB-SPE cartridge loading the second supernatant was subjected to elution with 1 mL of pure water. the effluents from loading the second supernatant and the effluents from the subsequent elution were combined to obtain a purified solution.

The purified solution and the absolute ethanol were mixed at a volume ratio of 1:2, centrifuged at 10,000 rpm for 20 min. A resulting supernatant was discarded, and a resulting precipitate was collected as polysaccharide.

The collected precipitate was redissolved by adding 5 mL of purified water thereto, and then freeze-dried. After that, as described in Example 3, the resulting system was subjected to methylation and glycoside residue derivatization in sequence, and glycosidic bond compositions of the polysaccharide were detected by liquid chromatography-mass spectrometry (LC-MS) in MRM mode.

In this example, the fermentation broth was a feces fermentation broth of pectin derived from mulberry bark (PMB) of citrus unshiu Marcovitch. After 12 h and 24 h of fermentation, the main glycosidic bond types of the extracted polysaccharide are 3-Rha, x-Rha, T-Ara, 2-Glc, 4-Glc, 6-Glc, 4-Gal, and 4,6-Gal. There is a difference in the glycosidic bond content of the polysaccharide extracted after fermentation for 12 h and 24 h, which is related to the consumption of carbohydrates by intestinal flora, indicating that the extraction method according to the present disclosure could effectively extract polysaccharides in the fermentation broth, but the metabolism of carbohydrates by intestinal flora was not further explained here.

The above descriptions are merely preferred embodiments of the present disclosure. It should be noted that a person of ordinary skill in the art may further make several improvements and modifications without departing from the principle of the present disclosure, but such improvements and modifications should be deemed as falling within the scope of the present disclosure.

What is claimed is:

1. A method for extracting and identifying a polysaccharide from a complex sample, comprising the following steps:

subjecting a complex sample to be treated to sterilization and enzyme deactivation to obtain a system, and subjecting the system to solid-liquid separation to obtain a sterilization and enzyme deactivation-treated solution, the complex sample to be treated being selected from the group consisting of feces, a fermentation broth, and a medium;

deproteinizing the sterilization and enzyme deactivation-treated solution to obtain a deproteinized solution;

purifying the deproteinized solution by using a hydrophilic lipophilic balance-solid phase extraction (HLB-SPE) cartridge to obtain a purified solution;

subjecting the purified solution to alcohol precipitation to obtain the polysaccharide; and subjecting the polysaccharide to methylation, glycoside residue derivatization and liquid chromatography-mass spectrometry (LC-MS) analysis in sequence.

2. The method of claim 1, wherein the sterilization and enzyme deactivation is conducted at a temperature of 95° C. to 105° C. for 10 min to 20 min.

3. The method of claim 1, wherein under the condition that the complex sample to be treated is the feces, the sterilization and enzyme deactivation is conducted in the presence of high-temperature-resistant α-amylase.

4. The method of claim 1, wherein the deproteinizing is conducted 3 to 6 times by a Sevag method; and a Sevag reagent for the deproteinizing is a mixture of chloroform and n-butanol at a volume ratio of (4-5):1.

5. The method of claim 1, wherein the purifying is conducted by a process comprising: loading the deproteinized solution onto the HLB-SPE cartridge, and then conducting elution by using water; and combining a first effluent obtained by the loading and a second effluent obtained by the elution to obtain the purified solution; and a volume ratio of the deproteinized solution to the water for the elution is in a range of 5:(0.5-1.5).

6. The method of claim 1, wherein an alcohol reagent for the alcohol precipitation is absolute ethanol, and a volume ratio of the purified solution to the absolute ethanol is in a range of 1:(2-4).

7. The method of claim 1, wherein a methylation reagent for the methylation is methyl iodide; the methylation is conducted in the presence of NaOH-dimethyl sulfoxide suspension; and a ratio of the polysaccharide, the NaOH-dimethyl sulfoxide suspension and the methyl iodide is in a range of 100 ng:(100-300) μL:(50-60) μL.

8. The method of claim 1, wherein the methylation is conducted 4 to 5 times; and the methylation is conducted at a temperature of 15° C. to 35° C. for 70 min to 90 min each time.

9. The method of claim 1, wherein the glycoside residue derivatization is conducted by a process comprising subjecting a resulting product from the methylation to hydrolysis reaction and derivatization reaction in sequence; the hydrolysis reaction is conducted in the presence of a trifluoroacetic acid aqueous solution; and a derivatization reagent for the derivatization reaction is 1-phenyl-3-methyl-5-pyrazolone.

10. The method of claim 9, wherein the hydrolysis reaction is conducted at a temperature of 105° C. to 110° C. for 6 h to 7 h; and the derivatization reaction is conducted at a temperature of 60° C. to 65° C. for 20 min to 25 min.

11. The method of claim 2, wherein under the condition that the complex sample to be treated is the feces, the sterilization and enzyme deactivation is conducted in the presence of high-temperature-resistant α-amylase.

12. The method of claim 7, wherein the methylation is conducted 4 to 5 times; and the methylation is conducted at a temperature of 15° C. to 35° C. for 70 min to 90 min each time.

* * * * *